United States Patent [19]

Siedle et al.

[11] Patent Number: 5,416,177

[45] Date of Patent: May 16, 1995

[54] TRIS(PENTAFLUOROPHENYL)BORANE COMPLEXES AND CATALYSTS DERIVED THEREFROM

[75] Inventors: Allen R. Siedle, Lake Elmo; William M. Lamanna, Stillwater, both of Minn.

[73] Assignee: Minnesota Mining and Manufacturing Company, St. Paul, Minn.

[21] Appl. No.: 282,820

[22] Filed: Jul. 29, 1994

Related U.S. Application Data

[60] Continuation of Ser. No. 99,197, Jul. 29, 1993, abandoned, which is a division of Ser. No. 868,041, Apr. 14, 1992, Pat. No. 5,296,433.

[51] Int. Cl.⁶ ............................................. C05F 4/76
[52] U.S. Cl. ...................................... 526/126; 526/134; 526/239; 526/279; 526/308; 526/336; 526/348.3; 526/348.4; 526/348.5; 526/352
[58] Field of Search ................................. 526/134, 126

[56] References Cited

U.S. PATENT DOCUMENTS

| | | | |
|---|---|---|---|
| 3,558,718 | 1/1971 | Gross | 260/606.5 |
| 4,219,681 | 8/1980 | Schwenk et al. | 568/842 |
| 4,404,344 | 9/1983 | Sinn et al. | 526/160 |
| 5,096,867 | 3/1992 | Canich | 502/103 |
| 5,191,132 | 3/1993 | Patsidis et al. | 585/375 |

FOREIGN PATENT DOCUMENTS

| | | |
|---|---|---|
| 2027145 | 4/1991 | Canada . |
| 2067525 | 4/1992 | Canada ............ C07F 7/00 |
| 0277003A1 | 8/1988 | European Pat. Off. . |
| 0277004A1 | 8/1988 | European Pat. Off. . |
| 0418044A2 | 3/1991 | European Pat. Off. . |
| 0426044A2 | 3/1991 | European Pat. Off. . |
| 0426637A2 | 5/1991 | European Pat. Off. . |
| 0426638A2 | 5/1991 | European Pat. Off. . |
| 0443739A1 | 8/1991 | European Pat. Off. . |
| WO93/12151 | 12/1992 | WIPO . |

OTHER PUBLICATIONS

Hlatky et al., J. Am. Chem. Soc. 1989, 111, 2728.
Yang et al., J. Am. Chem. Soc. 1991, 113, 3623.
Skupinska, Chem. Rev. 1991, 91, 613.
Samuel et al., J. Am. Chem. Soc., 1973, 9, 6263.
Kaminsky et al., Makromol. Chem., Rapid Commun., 1990, 11, 89–94.
Samuel et al., J. Organomet. Chem., 1976, 113, 331.
Shiono et al., Makromol. Chem., Rapid Commun., 1990, 11, 169–175.
Shock et al., J. Am. Chem. Soc., 1988, 110, 7701.
Pohlman et al., Pentafluorophenyl–Metal Chemistry III, 20 b, 5–11, 1965.
Massey et al., J. Organometal. Chem., 2 (1964) 245–250.
Kaminsky et al., Angew. Chem. Int. Ed. Engl. 28 (1989) Nr. 9.
Siedle et al., Amer. Chem. Soc., 1985, 0020-1669/85/1324-2216.
Siedle et al., Jour. of Organomet. Chem., 246 (1983) 83–93.

*Primary Examiner*—Mark Nagumo
*Attorney, Agent, or Firm*—Gary L. Griswold; Walter N. Kirn; Carolyn V. Peters

[57] ABSTRACT

Tris(pentafluorophenyl)borane complexes having the general formula $(C_6F_5)_3B \cdot (YXH)_q$ wherein X is oxygen, or sulfur; q is i to 3; Y is a hydrogen atom, $R^1$—, $(R^2)_3Si$—, or $(R^3)_2C=N$—; $R^1$ is a hydrocarbyl group containing 1 to 500 carbon atoms, and may contain a divalent oxygen and further may be a fluorine-containing hydrocarbyl group; $R^2$ is independently a linear or branched alkyl group containing 1 to 25 carbon atoms, or a phenyl group, further $R^2$ may contain a SiO— group; and $R^3$ is independently a hydrocarbyl group containing 1 to 25 carbon atoms, $R^3$ may be a hydrogen atom provided both $R^3$ groups selected are not hydrogen atoms; and to complexes containing the borane complexes with an organometallic compound, either as a neutral compound or as an acidic salt that are useful as catalysts for polymerization and copolymerization of olefins and to polymeric products prepared using these catalysts.

8 Claims, No Drawings

TRIS(PENTAFLUOROPHENYL)BORANE COMPLEXES AND CATALYSTS DERIVED THEREFROM

This is a continuation of application Ser. No. 08/099,197, filed Jul. 29, 1993, now abandoned, which is a division of application Ser. No. 07/868,041, filed Apr. 14, 1992, now U.S. Pat. No. 5,296,433.

FIELD OF THE INVENTION

This invention relates to complex compounds of tris(pentafluorophenyl)borane and to mixtures containing the borane complexes and an organometallic complex that are useful as catalysts for polymerization and copolymerization of olefins and to polymeric products prepared using these catalysts.

BACKGROUND OF THE INVENTION

Use of soluble Ziegler-Natta type catalyst systems in the polymerization of olefins, in particular polymerization of ethylene to polyethylene is known in the art. In general, traditional Ziegler-Natta type systems comprise a transition metal halide activated to form a catalyst species by reaction with a metal alkyl cocatalyst, particularly aluminum alkyl cocatalysts. However, aluminum alkyl cocatalysts are often used in large excess, see U.S. Pat. No. 4,404,344. This is disadvantageous because the aluminum compounds must be removed from the resultant polymers. These traditional Ziegler-Natta catalysts often contain a variety of different active sites, each of which has its own rate of initiation, propagation, and termination. As a consequence of this non-uniformity of active sites, the linear polyethylene has a broad molecular weight distribution. See for example, Comprehensive Organometallic Chemistry; Wilkinson, G., Ed.; Pergamon Press: Oxford, 1982; Vol. 3, Chapter 22.5, p 475; Transition Metals and Organornetallics as Catalysts for Olefin Polymerization; Kaminsky, W. and Sinn, H., Eds.; Springer-Verlag: New York, 1988, and Transition Metal Catalyzed Polymerizations: Alkenes and Dienes; Quirk, R. P., Ed.; Harwood: New York 1983.

Recently, catalysts have been reported that rely on boron rather than on aluminum-containing compounds. Boron-based catalysts, in contrast, to the aluminum-based catalysts are often stoichiometric in boron. That is, they contain one mole of boron-containing component per mole of transition metal. Furthermore, it is usually unnecessary to remove the small amount of boron from the polymer, unlike the aluminum-based catalysts, mentioned above.

Tris(pentafluorophenyl)borane $(C_6F_5)_3B$ forms 1:1 complexes with Lewis bases such as ether, amines, and phosphines. The compound is hygroscopic and, presumably forms a monohydrate but neither the composition, that is stoichiometry of this hydrate nor its properties have been disclosed. No uses for these donor-acceptor complexes have been taught, see Massey et at. J. Organomet. Chem. 1964, 2, 245. Hygroscopic $(C_6F_5)_3B \cdot Et_2O$ was reported by Pohlman et al. Z. Nat. 1965, 20b, 5.

Hlatky et al. J. Am. Chem. Soc. 1989, 111, 2728 described zwitterionic catalysts such as $(Me_5Cp)_2Zr[(m-C_6H_4)BPh_3]$. EPO 0 277 004 describes catalysts prepared by reacting, $(Me_5Cp)_2ZrMe_2$ with $B_9C_2H_{13}$, $[Bu_3NH][(B_9C_2H_{11})_2Co]$ or $[Bu_3NH][B_9C_2H_{12}]$. Alternatively, ammonium salts of $B(C_6F_5)_4$— may be used, WO 91 02,012; Chem. Abstr. 1991, 114, 247980u.

Similarly, EPO 0 418044 describes monocyclopentadienyl complex catalysts containing a non-coordinating, compatible anion such as $(C_6F_5)_4B$—. More recently, homogeneous catalysts exemplified by $[Cp_2ZrMe][MeB(C_6F_5)_3]$ have been synthesized from the reaction of $Cp_2ZrMe_2$ and $(C_6F_5)_3B$ see X. Yang et at. J. Am. Chem. Soc'y 1991, 113, 3623.

Furthermore, the above described catalysts are sparingly soluble in toluene. The catalysts are even less soluble in normally liquid $\alpha$-olefins such as 1-hexene or in mixtures of such olefins and non-reactive solvents, such as hexane, toluene or xylene. These catalysts generally separate as oils from toluene or toluene-hexane mixtures. Even though catalysis still proceeds, phase separation is undesirable for several reasons, for example contact between monomer and catalyst is less efficient when the catalyst is only partially soluble. When the catalyst is incompletely soluble, catalyzed polymerization typically takes place at different rates either in solution or at the solid-liquid interface, thus tending to lead to a broad distribution of polymer molecular weights. Furthermore, catalyst:monomer ratio in solution is generally difficult to control when the catalyst is only partially soluble.

It is further known that a soluble or molecularly dispersed catalyst typically permits more ready access of the substrate to the active sites. As a result, more efficient use of the catalyst is possible. It is also recognized that the molecular weight of a polymer is proportional to the concentration of monomer in the reaction mixture in which it is synthesized. Generally, high molecular weight is desirable in applications such as glues and adhesives, as well as in the construction of rigid objects such as gaskets, insulators and packaging materials.

Catalytic polymerization of lower olefins, in particular ethylene and propylene is relatively easy. On the other hand polymerization of longer chain $\alpha$-olefins tends to be slower and the products are often oligomers rather than high polymers, see Skupinska Chem. Rev. 1991, 91, 635. Heterogeneous catalysts such as $TiCl_3/AlEt_3$, which produce higher molecular weight polymers from long-chain $\alpha$-olefins, lead to a broad range of molecular weights (high polydispersity index).

SUMMARY OF THE INVENTION

Briefly, in one aspect of the present invention catalyst precursor complexes are provided comprising tris(pentafluorophenyl)borane, $(C_6F_5)_3B$ and at least one complexing compound such as water, alcohols, mercaptans, silanols, and oximes. These neutral complexes may be converted to acidic salts of their conjugate bases by reaction with amines. The neutral complexes or acidic salts are reacted with Periodic Table Group IVB organometallic compounds to form catalytically active compounds (hereinafter also referred to as catalysts) useful for polymerization of olefin monomers. Advantageoulsy, the catalysts of the present invention are soluble in olefins to the extent of $1 \times 10^{-3}$ molar (M) or greater. Catalysts that can function in undiluted monomer, as distinguished from monomer dissolved in inert diluent, are desirable because the catalysts and monomers tend to produce products having higher molecular weight. Additionally, because only low levels of the catalysts are used, removal of catalyst or its components from the final, product polymer is generally not required.

Catalysts of the present invention may be used to prepare poly-olefins from olefinically unsaturated monomers having 2 to 30, preferably 5 to 10 carbon atoms. The resulting polymers have a weight average molecular weight of 100,000 to 5,000,000, preferably 500,000 to 3,500,000 and have a polydispersity (PD) of molecular weights $\leq 3.5$, preferably 1.5 to 3. Polymers prepared from long chain α-olefins having high molecular weight and low polydispersibility are not previously described.

Suitable olefinically unsaturated monomers that may be polymerized using the catalysts of the present invention include, but are not limited to, linear- and branched α-olefins, cyclic olefins, olefins containing an aromatic group such as phenyl, olefins containing silicon and boron, and diolefins. Mixtures of these of monomers, as well as mixtures containing olefins and diolefins may be copolymerized. Preferred unsaturated monomers include linear α-olefins having the general formula $C_nH_{2n}$, where n is 5 to 10.

A feature of the present invention is the incorporation of anions of the type $YX-B(C_6F_5)_3-$ into novel complex salts of Group IVB transition metals (titanium, zirconium, and hafnium), to produce highly active catalysts capable of polymerizing longer chain poly-α-olefins to yield products having very high molecular weights and a narrow polydispersity index. Furthermore, preparation of these salts are described, and such salts can either contain or are essentially free of Lewis bases. An additional feature of this invention is the incorporation of flat carbocyclic ligands into these novel complex salts, to produce olefin polymers of exceptionally high molecular weight. Thus, as shown below using $[(ligand)_2ZrMe][(C_6F_5)_3BOC_{18}H_{37}]$ as the catalyst and 1-hexene as the monomer, polymer molecular weight increases as the ligand is changed in the order of cyclopentadienyl<indenyl<<fluorenyl. The fluorenyl ligand is therefore particularly useful when high molecular weight, rubbery polyolefins are desired.

In this application:
"Cp" means a carbocyclic ligand, such as cyclopentadienyl, indenyl or fluorenyl;
"Me" means a methyl group;
"Et" means an ethyl group;
"Bu" means a butyl group;
"Ph" means a phenyl group;
"hydrocarbyl" is used in its usual sense to mean a group containing hydrogen and carbon atoms, such as alkyl, alkenyl, aryl, cycloalkyl, cycloalkenyl, alkaryl, arylalkyl, and the like; and
"Group IVA" and "Group IVB" are the Periodic Table CAS version designations.

DETAILED DESCRIPTION OF THE PREFERRED EMBODIMENT

The compound $(C_6F_5)_3B$, tris(pentafluorophenyl)borane (also referred to as tris(pentafluorophenyl)boron), forms Lewis base complexes with a wide variety of alcohols, mercaptans, silanols, and oximes. These borane complexes are catalyst precursors that when combined with Group IVB organometallic compounds produce catalysts useful for polymerization of olefins, such that the polymers have high molecular weights and low polydispersities, that is a narrow molecular weight distribution.

Lewis base complexes of $(C_6F_5)_3B$ bearing at least one acidic hydrogen atom on the boron-bound heteroatom are useful for preparing catalysts. These compounds can be represented by the general formula: $(C_6F_5)_3B.(YXH)_q$ wherein X, Y and q are as described below and the valence of X is completed with hydrogen atoms where necessary to provide a neutral compound.

The following reaction scheme illustrates how neutral Lewis base complexes of tris(pentafluorophenyl)borane and corresponding acidic salts may be prepared. For illustration purposes, the reaction scheme depicts $(C_2H_5)_3N$ as a reactant to produce acidic salts. Without intending to be bound by theory, reaction scheme further illustrates how the neutral Lewis base complexes of tris(pentafluorophenyl)borane and the corresponding acidic salts are believed to react with Group IVB organometallic complexes to produce the catalytically active salts of this invention.

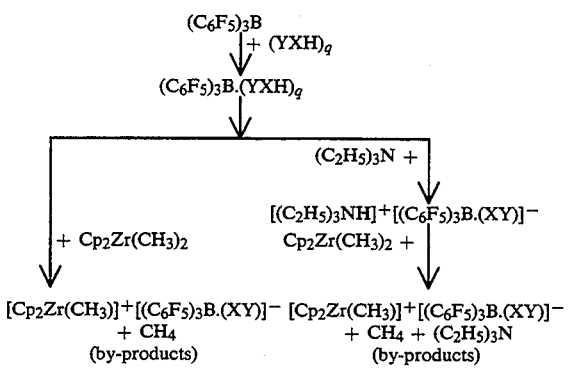

wherein Y, X, and q are as define below

The neutral borane complexes have the general formula $$(C_6F_5)_3B.(YXH)_q \qquad (I)$$

wherein X is oxygen, or sulfur;
q is 1 to 3, preferably q is 1;
Y is a hydrogen atom, $R^1-$, $(R^2)_3Si-$ or $(R^3)_2C=N-$;
$R^1$ is a hydrocarbyl group containing 1 to 500, preferably 1 to 100 carbon atoms, and may contain a divalent oxygen and further may be a halogen-containing hydrocarbyl group, for example the $R^1$ group can be $CH_3OC_2H_4-$, t-butylcyclohexyl, isopropyl, allyl, benzyl, methyl, ethyl, $C_{18}H_{37}$, oligomeric poly-α-olefins (containing 2 to 100 monomeric units), or $CF_3CF_2(C_2F_4)_nC_2H_4-$, where n has an average value of 3.5;
$R^2$ is independently a linear or branched alkyl group containing 1 to 25 carbon atoms, or a phenyl group, further $R^2$ may contain a SiO— group, for example $(R^2)_3$ may be $(t-C_4H_9)(CH_3)_2-$ or $((CH_3)_3SiO)_3-$; and
$R^3$ is independently a hydrocarbyl group containing 1 to 25 carbon atoms, further $R^3$ may be a hydrogen atom provided both $R^3$ groups selected are not hydrogen atoms, for example when X is oxygen, $(R^3)_2C=NOH$ forms oximes, a compound (either cis or trans) containing the oxime group $=C=NOH$, and is a condensation product of aldehydes or ketones with hydroxylamine.

Tris(pentafluorophenyl)borane tends to form complexes with alcohols having the general formula $R^1OH$. For example, treatment of $(C_6F_5)_3B$ with methanol liquid or vapor produces the bis(solvate) $(C_6F_5)_3B.2MeOH$. No significant amount of methanol can be removed by pumping at room temperature. This compound can be converted to $(C_6F_5)_3B.MeOH$ by treatment with one equivalent of $(C_6F_5)_3B$. The 1:1 complex $(C_6F_5)_3B.MeOH$ may also be prepared by reacting $(C_6F_5)_3B$ with one equivalent of methanol. Isopropanol forms a bis(solvate) as well but one equivalent of alcohol is removed under vacuum at room temperature.

Tris(pentafluorophenyl)boron complexes of less volatile alcohols can be prepared by combining one equivalent each of an alcohol and $(C_6F_5)_3B$ in a suitable, non-reactive solvent such as chloroform or toluene, followed by evaporation of the solvent. Suitable alcohols contain a wide variety of aliphatic or aromatics groups including but not limited to linear (stearyl alcohol), cyclic (t-butylcyclohexanol), branched (isopropanol), unsaturated (allyl alcohol), aromatic (benzyl alcohol), optically active (menthol), oxygen-substituted ($MeOC_2H_4OH$), oligomeric (poly-1-hexene alcohol), and halogen-substituted $[CF_3CF_2(C_2F_4)_nC_2H_4OH]$, where n has an average value of 3.5.

Suitable alcohols generally have pKa values between $-2$ and $-4$. For example, 2,2,2-trifluoroethanol and phenol do not form isolable complexes. Formation of a stable complex is readily ascertained by boron nuclear magnetic resonance ($^{11}B$ NMR) spectroscopy. The $(C_6F_5)_3B$ complexes of this invention have chemical shifts between $-5$ and $+15$ ppm (relative to external $BF_3.OEt_2$) compared with $+60$ ppm for the starting material $(C_6F_5)_3B$.

Other specific examples of $(YXH)_q$ (when q is 1) include silanols $((R^2)_3SiOH)$, mercaptans $(R^1SH)$, and oximes $((R^3)C=NOH)$. Examples of silanols include but are not limited to $(t-C_4H_9)Me_2SiOH$ and $(Me_3SiO)_3SiOH$. Higher mercaptans having low vapor pressures are preferred in catalyst applications such that the polymers produced do not have an objectionable odor. An example of a mercaptan useful in the present invention is octadecyl mercaptan. Examples of oximes include acetone oxime and cyclohexanone oxime.

Of the class of compounds of the type $(C_6F_5)_3B.(YXH)_q$, when Y is hydrogen, X is oxygen, and q is 1 or 3, the complex with water is a special case. Exposure of anhydrous $(C_6F_5)_3B$ to water vapor, produces $(C_6F_5)_3B.3H_2O$, a white, stable solid. No intermediate hydrate was detected by infrared spectroscopic analysis. The water content was demonstrated by a single crystal X-ray structure determination. Formation of a trihydrate was unexpected because all other previously known $(C_6F_5)_3B$ complexes with Lewis bases have a 1:1 stoichiometry. Vacuum sublimation of the trihydrate produced a mixture of the monohydrate and $(C_6F_5)_3B$. The pure monohydrate, $(C_6F_5)_3B.H_2O$, however may be obtained by combining in organic solvents, such as toluene or chloroform, one equivalent of $(C_6F_5)_3B.3H_2O$ with two equivalents of $(C_6F_5)_3B$ followed by evaporation of the solvent. This conproportionation reaction is a convenient way of synthesizing the monohydrate as needed. Unlike $(C_6F_5)_3B.3H_2O$, $(C_6F_5)_3B.H_2O$ is unstable and slowly decomposes, either in solution or in the solid state, to $(C_6F_5)_2BOH$ and $C_6F_5H$. The monohydrate may also be prepared by combining one mole each of water and $(C_6F_5)_3B$.

The heteroatom-bound protons in Lewis base complexes of $(C_6F_5)_3B$, such as $(C_6F_5)_3B.R^1OH$ and $(C_6F_5)_3B.R^1SH$ are acidic and can be removed by treatment with bases such as primary, secondary, or tertiary amines. For example, reaction of $(C_2H_5)_3N$ with $(C_6F_5)_3B.3H_2O$ or $(C_6F_5)_3B.2CH_3OH$ produces the acidic salts $[C_2H_5)_3NH]^+[(C_6F_5)_3BOH]^-$ and $[Et_3NH]^+[(C_6F_5)_3BOCH_3]^-$ respectively. Preferred bases are triethylamine, tributylamine and N,N-dimethylaniline.

Catalysts useful for polymerization of olefinic hydrocarbons may be prepared using the precursor borane complexes and hydrocarbylcyclopentadienyl metal complexes having the general formula:

$$(Cp)_pM(R^4)_{4-p} \qquad (II)$$

wherein M is titanium, zirconium or hafnium;
p is 1 or 2
Cp is a cyclopentadienyl ligand, wherein each carbon atom in the ring may be, independently, substituted with a radical selected from the group consisting of hydrocarbyl radicals, hydrocarbyl-substituted metalloid radicals wherein the metalloid is selected from Group IVA of the Periodic Table of the elements wherein the hydrocarbyl and substituted-hydrocarbyl radicals contain 1 to 20 carbon atoms and can include straight and branched alkyl groups, cyclic hydrocarbon groups, alkyl-substituted cyclic hydrocarbon groups, aromatic groups or alkyl-substituted aromatic groups; one or two pairs of adjacent hydrogen atoms of the cyclopentadienyl ligand may be substituted with one or two $-(CH)_4$ groups to form indenyl or fluorenyl radicals, respectively; further, compounds in which one or two methylene rings having the general formula $(CH_2)_n$ wherein n is 3 to 6 may be substituted for two adjacent hydrogen groups in the cyclopentadienyl ligand; further, when p is 2, the cyclopentadienyl ligands may be combined into one bidentate ligand molecule by connecting the cyclopentadienyl ligands by an organic or organometalloid group; and $R^4$ is independently hydrogen or a hydrocarbyl or substituted-hydrocarbyl group containing from 1 to 20 carbon atoms and may be a straight or branched alkyl group, and if sufficiently large enough, a cyclic hydrocarbyl group, an alkyl-substituted cyclohydrocarbyl group, an aromatic group, an aromatic-substituted alkyl group (e.g., benzyl), or an alkyl-substituted aromatic group and also include trisubstituted organometalloid groups of Group IVA elements wherein each hydrocarbyl group on the metalloid contains from 1 to 20 carbon atoms.

Suitable examples of Cp include but are not limited to cyclopentadienyl, indenyl, fluorenyl, bis(octahydrofluorenyl), 1,2-bis(1-indenyl)ethane, 1,2-bis(tetrahydroindenyl)ethane, isopropyl(cyclopentadienyl-1-fluorenyl) and 1,3-bis(9-fluorene)propane. Chiral metallocenes are also suitable and useful when a stereoregular polymer is desired. General structures of cyclopentadienyl, indenyl and fluorenyl ligands, respectively are represented below.

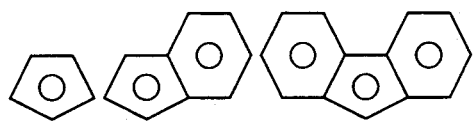

While not intending to be bound by theory, the organometallic complex, $(Cp)_pM(R^4)_{4-p}$ is believed to react with acid salts of the anions, such as $(C_6F_5)_3B.OR^{1-}$, $(C_6F_5)_3B.OH^-$, $(C_6F_5)_3B.SR^{1-}$, $(C_6F_5)_3B.OSi(R^2)_3^-$ or $(C_6F_5)_3B.ON=C(R^3)_2^-$ (containing at least one acid proton in the cationic portion of the salt) to form byproducts and catalytically active salts containing $(Cp)_pM(R^4)_{3-p}{}^+$. For example, this can be illustrated by the following reaction with $[Et_3NH][(C_6F_5)_3BOH]$.

(Reaction Scheme I)

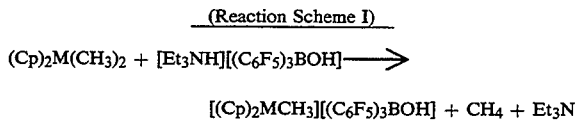

$[(Cp)_2MCH_3][(C_6F_5)_3BOH] + CH_4 + Et_3N$

Alternatively, the need for an acidic salt can be by-passed in the direct reaction of the metal complexes with neutral complexes of tris(pentafluorophenyl)borane with water, alcohols, mercaptans, silanols or oximes. For example, (Reaction Scheme II)

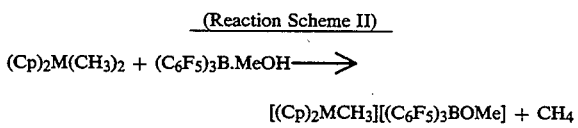

$[(Cp)_2MCH_3][(C_6F_5)_3BOMe] + CH_4$

Materials prepared by either route can be used as catalysts for the polymerization of olefins. Importantly, catalysts prepared according to Reaction Scheme II can be obtained free of extraneous Lewis base byproduct such as triethylamine (obtained in Scheme I).

Materials described in this invention are useful for polymerization of olefins such as ethylene and propylene and in particular higher olefins, for example, 1-hexene or 1-octene. Polyolefins having high weight average molecular weights may be prepared by treating undiluted olefins with a catalytically effective amount of a catalyst of the present invention. Optionally, the polyolefins may be diluted with an inert diluent, such as toluene or hexane.

Catalysts of the present invention may be used to prepare poly-olefins from olefinically unsaturated monomers having from 2 to 30, preferably 5 to 10 carbon atoms. The resulting polymers have a weight average molecular weight of 100,000 to 5,000,000, preferably 500,000 to 3,500,000 and have a polydispersity (PD) of molecular weights $\leq 3.5$, preferably 1.5 to 3. Polymers prepared from longer chain olefins, for example, $C_nH_{2n}$ ($n\geq 5$) olefins having high molecular weight and low polydispersity have not been previously described.

Olefinically unsaturated monomers that may be polymerized using the catalysts of the present invention include, but are not limited to, linear- and branched α-olefins, cyclic olefins, olefins containing an aromatic group such as phenyl, olefins containing silicon or boron, and diolefins. Mixtures of these of monomers, as well as mixtures containing olefins and diolefins may be copolymerized.

TABLE 1

Polyhexenes Obtained with Different Metallocenium Ion Catalysts[a]

| Initiator | Degree of Polymerization[b] | % Conversion |
|---|---|---|
| $Cp_2ZrMe^+$ | 99 | 100 |
| $(indenyl)_2ZrMe^+$ | 200 | 70 |
| $(Me_5Cp)_2ZrMe^+$ | 83 | 100 |
| $[(Me_3Si)_2Cp]_2HfMe^+$ | 66 | 51 |
| $(Me_5Cp)_2HfMe^+$ | 118 | 100 |
| $(Me_3SiCp)_2HfMe^+$ | 60 | 98 |
| $(Me_3SiCp)_2HfMe^{+(c)}$ | 56 | 90 |

TABLE 1-continued

Polyhexenes Obtained with Different Metallocenium Ion Catalysts[a]

| Initiator | Degree of Polymerization[b] | % Conversion |
|---|---|---|
| $Cp_2HfMe^+$ | 429 | 100 |
| $Cp_2HfMe^{+(d)}$ | 506 | 100 |
| $(indenyl)_2HfMe^+$ | 1025 | 100 |
| $(Me_3SiCH_2Cp)_2ZrMe^+$ | 19 | 4 |
| $(n\text{-}C_8H_{17}Cp)_2HfMe^+$ | 23 | 94 |
| $(Me_3SiCp)_2ZrMe^+$ | 10 | 55 |
| $[Me_2Si(C_5H_4)_2]ZrMe^+$ | 4 | <1 |
| $(PhCH_2SiMe_2Cp)_2ZrMe^+$ | 7 | 88 |
| $(fluorenyl)_2ZrMe^+$ | 4800 | 69 |
| $[(indenyl)_2C_2H_4)]ZrMe^+$ | 156 | 87 |
| $[(indenyl)_2C_2H_4)]HfMe^+$ | 271 | 78 |

[a]Conditions: $C_{18}H_{37}O.B(C_6F_5)_3{}^-$ salts in 0.5 mL toluene-1-hexene, monomer: catalyst 6400:1 at 0° C.
[b]determined by $^1H$ NMR analysis and refers to the average number of monomer units in the polymer chain
[c]anion is $C_{18}H_{37}S.B(C_6F_5)_3{}^-$
[d]anion is conjugate base of polyhexene alcohol.$B(C_6F_5)_3$ Ring substitution on the Cp ligand in the catalysts of the present invention can lead to reduced polymer molecular weight and activity. This is illustrated in Table 1. Reduction of polymer molecular weight is generally undesirable in many applications since it is associated with loss of polymer cohesive strength. For example, decreases in molecular weight associated with the $Me_3Si$ group has not been described before. It is surprising because catalysts prepared from $(Me_3SiCp)_2ZrMe_2$ and methyl aluminoxane tend to produce higher molecular weight polyhexene than does unsubstituted $Cp_2ZrMe_2$.

An advantage of the present invention is the permissible introduction of solubilizing groups that enhance solubility of catalyst salts in the olefinic monomer or solution of monomer and solvent into the anion rather than the cation that contains the active catalytic site. The solubilizing groups are spatially removed from the active site, and therefore do not interfere with polymerization and thus produce polymers of high molecular weight. For example, the catalyst $[(indenyl)_2ZrMe)][(C_6F_5)_3B.OC_{18}H_{37}]$, in which the anion contains the solubilizing octadecyl group that was introduced via of the alcohol complex $(C_6F_5)_3B.C_{18}H_{37}OH$, is soluble to the extent of about $10^{-3}M$ in 80:1 (v/v) 1-hexene-toluene. In an other example, polyhexene alcohol having an average degree of polymerization of 5.9 and bearing a terminal $CH_2OH$ group, yielded a solution as concentrated as $10^{-3}M$ in 40:1 hexene-hexane. For example, the structure of the solubilizing group can be varied so as to produce good catalyst solubility in a monomer of choice by suitably modifying the structure of $R^1OH$ in $(C_6F_5)_3B.R^1OH$. As illustrated in the examples below, the anions of the present invention provide catalysts that produce higher molecular weight polyolefins than superficially related catalysts, even at equivalent monomer:catalyst ratios.

Although $(indenyl)_2ZrMe_2$ organometallic compounds are reportedly useful in the preparation of catalysts, there appears to be no correlation between the structure of the ligand(s) in the organometallic portion of the catalyst and the molecular weights of polymers of higher olefins ($C_5$ and greater) produced with such catalysts. As a result, it is not readily apparent which organometallic compounds may be used to prepare high molecular weight polymers. For example, the soluble, homogeneous olefin polymerization catalysts described by U.S. Pat. No. 4,404,344 (Kaminsky et al.) when used to prepare poly(hexene), produces oligomers having molecular weights less than 50,000.

Structurally, flat cyclopentadienyl ligands, when incorporated into these complex salts, produce polymers of high molecular weight. As shown in Table 1 above, using [(ligand)$_2$ZrMe][(C$_6$F$_5$)$_3$B.OC$_{18}$H$_{37}$] as the catalyst and 1-hexene as the monomer, the degree of polymerization in the product polymer increased from 99 to 200 to 4800 as the ligand was changed in the order from cyclopentadienyl to indenyl to fluorenyl, respectively. The fluorenyl ligand is particularly useful when high molecular weight, rubbery polyolefins are desired.

Objects and advantages of this invention are further illustrated by the following examples, but the particular materials and amounts thereof recited in these examples, as well as other conditions and details, should not be construed to unduly limit the invention.

EXAMPLES

All compounds were characterized by at least one of infrared (IR) and nuclear magnetic resonance (NMR) spectroscopies. NMR analysis included $^1$H, $^{11}$B, $^{13}$C, and $^{19}$F. Number average molecular weight ($M_n$) and weight average molecular weight ($M_w$) for polymers having $M_w$ less than $10^6$ were determined by gel permeation chromatography (GPC) using polystyrene standards or by NMR analysis as is known to those skilled in this art. Polydispersity (PD) refers to the weight-average molecular weight divided by the number average molecular weight, that is, $M_w/M_n$.

Materials whose weight average molecular weight exceeded $10^6$ were characterized by low angle laser light scattering techniques as is known to those skilled in this art. All starting materials and solvents are commerical available or known in the literature, unless otherwise stated or apparent. All commercially available materials and solvents are available from Aldrich Chemical Co., unless otherwise noted.

PREPARATION EXAMPLE 1

Preparation of (C$_6$F$_5$)$_3$B

Tris(pentafluorophenyl)borane was prepared by the reaction of C$_6$F$_5$Li with BCl$_3$ in hexane at temperatures below $-50°$ C. according to the procedure described in Massey et al. J. Organomet. Chem. 1964, 2, 245.

EXAMPLE 1

Preparation of (C$_6$F$_5$)$_3$B.3H$_2$O

A 0.87 gram quantity of (C$_6$F$_5$)$_3$B was placed in one leg of a reactor consisting of an inverted U-tube, closed at both ends and fitted with a stopcock and 0-ting joint so that the apparatus could be connected to a vacuum line. Excess water was placed in the other leg. After the water had been frozen with a low temperature bath, the apparatus was evacuated. After warming the reactor to room temperature, the borane reacted with water vapor to form the trihydrate. After water uptake was completed, excess water was pumped away to provide the air-stable product in quantitative yield.

EXAMPLE 2

Preparation of (C$_6$F$_5$)$_3$B.H$_2$O

A mixture of 0.566 gram (1 mmol) (C$_6$F$_5$)$_3$B.3H$_2$O as prepared in Example 1 and 1.024 grams (2 mmol) (C$_6$F$_5$)$_3$B in 10 mL dichloromethane was stirred for 15 minutes and then evaporated to dryness under vacuum. A quantitative yield of the product remained and was stored under dry nitrogen.

EXAMPLE 3

Preparation of [Et$_3$NH][(C$_6$F$_5$)$_3$BOH]

A solution of 3.6 grams (C$_6$F$_5$)$_3$B.3H$_2$O as prepared in Example 1 in 20 mL toluene was treated with 0.76 gram triethylamine in 3 mL of the same solvent. The reaction mixture was diluted with 50 mL hexane to precipitate 2.75 gram of crude product. Using Karl Fisher analysis, the crude product was determined to be a hydrate and the % H$_2$O present was 0.66. The crude product was recrystallized by solution in a minimum amount of hot toluene, followed by cooling to $-50°$ C. Filtration and vacuum drying yielded a material containing 0.15 % H$_2$O (by weight), corresponding to 5 mole per cent H$_2$O.

EXAMPLE 4

Preparation of (C$_6$F$_5$)$_3$B.2MeOH

A solution of 0.34 gram of (C$_6$F$_5$)$_3$B in 1.5 mL methanol was prepared under dry N$_2$ and evaporated to dryness to yield a clear viscous residue that crystallized under dynamic vacuum (vacuum pumping) overnight. The yield was 0.33 gram.

EXAMPLE 5

Preparation of [Ph$_3$PMe][(C$_6$F$_5$)$_3$BOMe]

A solution of 0.39 gram (0.76 mmol) of (C$_6$F$_5$)$_3$B in 1 mL methanol was treated with a slight excess (>5%) of methanolic sodium methoxide. Excess methyltriphenylphosphonium bromide was then added to the solution. The solution was diluted to the cloud point with water and then refrigerated. White crystals were collected on a filter, washed with water and vacuum dried. The yield was 0.58 grams (93%),

EXAMPLE 6

A similar reaction to Example 5 was used to prepare the triethylammonium salt but, under these conditions, partial hydrolysis of the anion to (C$_6$F$_5$)$_3$BOH$^-$ occurred.

EXAMPLE 7

Preparation of (C$_6$F$_5$)$_3$B.C$_{18}$H$_{37}$OH

A solution of 0.135 gram (0.5 mmol) of 1-octadecanol and 0.256 gram (0.5 mmol) of (C$_6$F$_5$)$_3$B in 4 mL toluene was stirred for 30 minutes. The solution was then evaporated on a vacuum line. The remaining product was as a viscous oil, and the yield was approximately 0.37 gram. The (C$_6$F$_5$)$_3$B complex was prepared and handled in an atmosphere of dry nitrogen.

EXAMPLE 8

Preparation of (C$_6$F$_5$)$_3$B.C$_{18}$H$_{37}$SH

A solution of 0.143 gram (0.5 mmol) of 1-octadecyl mercaptan and 0.356 gram (0.5 mmol) of (C$_6$F$_5$)$_3$B in 5 mL dichloromethane was evaporated under high vacuum. The residual product was an oil weighing 0.36 gram.

EXAMPLE 9

Preparation of (C$_6$F$_5$)$_3$B.C$_4$H$_9$OC$_2$H$_4$OH

A solution of 0.059 gram (0.5 mmol) of 2-butoxyethanol, dried over 4A molecular sieves and 0.256 gram (0.5 mmol) of $(C_6F_5)_3B$ in 1 mL toluene was evaporated under high vacuum. The residual product was a viscous oil and the yield was approximately 0.24 gram.

EXAMPLE 10

Preparation of $(C_6F_5)_3B\cdot cyclo-C_6H_{10}=NOH$

A solution of 0.056 gram (0.5 mmol) of cyclohexanone oxime and 0.256 gram of $(C_6F_5)_3B$ in 2.5 mL dichloromethane was evaporated under high vacuum to leave 0.28 gram of product.

EXAMPLE 11

Preparation of $(C_6F_5)_3B\cdot(Me_3SiO)_3SiOH$

A solution of 0.3 12 gram (1 mmol) of tris(trimethylsiloxy)silanol (PCR, Inc., Gainesville, Fla.) and 0.512 gram (1 mmol) of $(C_6F_5)_3B$ in 1.5 mL toluene was stirred for 30 minutes and then evaporated under high vacuum. There remaining 0.8 gram of product was a white semi-solid.

EXAMPLE 12

Fluorinated Alcohol Complex

Tris(pentafluorophenyl)borane (0.51 gram, 1 mmol) and 0.44 gram (1 mmol) of $CF_3CF_2(CF_2CF_2)_nCH_2CH_2OH$ (as prepared in U.S. Pat. No. 4,219,681, Example 1 and such description is incorporated herein by reference) in which the average value of n was 3.5 were combined under dry nitrogen in 2 mL of $CF_2ClCFCl_2$. After stirring the solution for approximately 1 hour, the solvent was evaporated to leave a fluorinated alcohol complex as a greasy solid.

EXAMPLE 13

Polymerization using $(C_6F_5)_3B\cdot H_2O$

1. Preparation of $(C_5H_5)_2ZrMe_2$ $(C_5H_5)_2ZrMe_2$ was prepared by treatment of $(C_5H_5)_2ZrCl_2$ in diethyl ether with two equivalents of methyllithium as described in Samuel et al. J. Am. Chem. Soc. 1973, 95:19, 6263.

2. 1-Hexene (0.67 gram) was added under nitrogen to a catalyst prepared by combining 0.05 mmole each of $(C_6F_5)_3B\cdot H_2O$ prepared according to Example 2 and $(C_5H_5)_2ZrMe_2$. After a few seconds, an exothermie reaction occurred and the mixture became thick. After approximately 50 minutes, any suspended catalyst was removed by centrifugation. Unreacted monomer was then evaporated. NMR ($^1H$) analysis showed that the resultant polymer had a number average molecular weight ($M_n$) of 400. The yield of polymer was 95%.

EXAMPLE 14

Polymerization using $(Me_5Cp)HfMe_3$

1. Preparation of $(Me_5C_5)HfMe_3$ $(Me_5C_5)HfMe_3$ was prepared by reacting $(Me_5C_5)HfCl_3$ with 3 equivalents of methyllithium as described in Schock et at. J. Am. Chem. Soc. 1988, 110, 7701.

2. A reaction similar to that in the Example 13 was carried out using $(Me_5C_5)HfMe_3$ instead of $(C_5H_5)_2ZrMe_2$. The yield of polymer, with an $M_n$ of 2200, was 90%.

EXAMPLE 15

Polymerization using $[Et_3NH][(C_6F_5)_3BOH]$

To 0.31 gram (0.5 mmol) of $[Et_3NH][(C_6F_5)_3BOH]$ (as prepared in Example 3) suspended in 6 mL toluene was added dropwise under dry nitrogen with stirring 0.13 gram (0.5 mmol) $(C_5H_5)_2ZrMe_2$ (as prepared in Example 13(1)) in 1 mL of the same solvent. Gas evolution occurred. The resulting orange oil that separated was removed by decantation, washed with toluene, then hexane, and vacuum dried to give 0.31 gram of catalyst as an orange foam.

This catalyst (0.01 gram) was added under dry nitrogen to 0.67 gram of 1-hexene. After 3 days, the reaction mixture was diluted with hexane and filtered to remove any undissolved catalyst. Evaporation of the hexane left 0.45 gram of polymer. Gel permeation chromatography (GPC) revealed that the product had $M_w=27,700$, $M_n=9100$ and PD=3.04.

EXAMPLE 16

Soluble Catalyst Prepared Using $(C_6F_5)_3B\cdot C_{18}H_{37}OH$

A solution of 0.05 mmol $C_{18}H_{37}OH$ in 0.3 mL toluene was added under dry $N_2$ to 0.05 mmol of $(C_6F_5)_3B$. Then, 0.05 mmol of $(C_5H_5)_2HfMe_2$ as prepared in Example 14 was added to the solution. Approximately, one half of the resulting catalyst solution was added with stirring to 13.4 gram dry, oxygen-free 1-hexene that had been cooled to 0° C., the monomer:catalyst ratio was 6400:1. The reaction mixture was essentially clear and transparent, that is, no suspended solids were observed. After approximately 16 hours, the polymer product was removed from the reactor by dissolution in hot heptane. After the heptane had been stripped at 95° C. using a water aspirator, 13.6 grams of polymer remained having $M_w=148,000$, $M_n=55,500$ and PD=2.67.

EXAMPLES 17(a) AND 17(b)

Reactions similar to Example 16 were carried out using the boron complex prepared according to Example 16 and (a) $(Me_3SiC_5H_4)_2HfMe_2$ was prepared by reacting $Li[Me_3SiC_5H_4]$ and $HfCl_4$ in tetrahydrofuran followed by alkylation with methyllithium. The monomer:catalyst ratio was 6400:1. The resulting polymer had an $M_n$ of 5040 as determined by NMR analysis; and (b) $(n-C_5H_{17}C_5H_4)_2HfMe_2$ was prepared by reacting $NaC_5H_5$ in liquid ammonia with $1-C_8H_{17}Br$ to provide $n-C_8H_{17}C_5H_5$. This was then convened by reaction with $n-C_4H_9Li$ and then $HfCl_4$ to provide $(n-C_5H_{17}C_5H_4)_2HfCl_2$. Subsequent alkylation with methyllithium produced $(n-C_5H_{17}C_5H_4)_2HfMe_2$. The monomer:catalyst ratio was 3200. The resulting polymer had an $M_n$ of 1932 as determined by NMR analysis.

EXAMPLE 18

Polymerization Using Oligomeric (Polyhexene) Alcohol

A reaction like that in Example 16 was carried out using an oligomeric (polyhexene) alcohol (average degree of polymerization 5.9) instead of octadecanol. The oligomeric (polyhexene) alcohol was prepared according to the procedure described in Examples 1a and 1b of co-pending U.S. patent application Ser. No. 07/865,940, filed Apr. 9, 1992 and such description is incorporated herein by reference. The yield of polymer was essentially quantitative. GPC analysis showed the polymer had $M_w=164,000$, $M_n=63,000$ and PD=2.6.

EXAMPLE 19

Comparative example using background art catalyst

Hexene was catalytically polymerized using [(C$_5$H$_5$)$_2$HfMe][MeB(C$_6$F$_5$)$_3$], similar to the Zr analogue described in Yang et al. J. Am. Chem. Soc. 1991, 113, 3623.

Cp$_2$HfMe$_2$ and (C$_6$F$_5$)$_3$B (0.025 mmol each) were combined in 0.7 mL anhydrous toluene in a dry nitrogen atmosphere. Reaction occurred and a yellow oil separated. The yellow oil was dispersed by shaking and added to 13.4 grams of dry, oxygen-free 1-hexene at 0° C. Separation of a solid catalyst phase was observed. After approximately 48 hours, the resultant polymer was removed from the reactor by dissolving it in hot cyclohexane. The polymer, after removing the solvents under water aspirator vacuum weighed 13.6 grams (some residual solvent was present). GPC analysis revealed that the polymer had M$_w$=48,000, M$_n$=13,500 and PD=3.55. The molecular weight of the polymer was lower, and the polydispersity higher than that of the material produced under similar conditions in Example 16.

EXAMPLE 20

Polymerization using (C$_6$F$_5$)$_3$B.C$_{18}$H$_{37}$SH

To a solution of 0.05 mmol of the 1-octadecyl mercaptan complex of (C$_6$F$_5$)$_3$B as prepared in Example 8 was added under nitrogen with stirring 0.024 gram (0.05 retool) of (Me$_3$SiCp)$_2$HfMe$_2$ in 0.1 mL anhydrous toluene. This mixture was then added to 13.4 grams of dry, oxygen-free 1hexene. After approximately 48 hours, the polymer was dissolved in heptane, and then filtered through a pad of granular alumina. After evaporation of the solvent under reduced pressure, there remained 10.2 grams of polymer having an M$_n$ of 4900 as determined by $^1$H NMR.

EXAMPLE 21

Polymerization using (C$_6$F$_5$)$_3$B.(MeSiO)$_3$SiOH

A toluene solution (0.3 mL) containing 0.025 mmol each (C$_6$F$_5$)$_3$B.(Me$_3$SiO)$_3$SiOH and (indenyl)$_2$HfMe$_2$ as prepared in Example 14 was added with stirring to 13.4 grams of dry, oxygen-free 1-hexene that had been cooled to 0° C. After approximately 16 hours at this temperature, the reactor was opened to air, a small amount of toluene was added and the resulting product scraped into a jar. After the volatiles were removed at 95° C. /6.7 hPa (5 mm Hg), 11.3 grams of polymer remained. The polymer had an M$_w$=340,000, M$_n$=145,000 and PD=2.34.

EXAMPLE 22

Polymerization using (C$_6$F$_5$)$_3$B.cyclo—C$_6$H$_{10}$=NOH

A suspension in 0.85 mL toluene of a catalyst prepared from 0.025 mmole each of the (C$_6$F$_5$)$_3$B—cyclohexanone oxime complex as prepared in Example 10 and (indenyl)$_2$HfMe$_2$ was added with stirring to 13.4 grams of cold (0° C.) dry, oxygen-free 1-hexene. After approximately 16 hours, the organic phase was removed and evaporated to give 1.2 grams of polymer having M$_n$ of 31,000 as determined by NMR analysis.

EXAMPLE 23

Polymerization using (C$_6$F$_5$)$_3$B.BuOC$_2$H$_4$OH

In 0.3 mL anhydrous toluene were combined 0.025 mmole each of the butoxyethanol complex as prepared in Example 9 and (indenyl)$_2$HfMe$_2$. Then 0.67 gram of 1-hexene was added. After approximately 16 hours, the reaction mixture was evaporated to give 0.44 gram (66%) of polymeric product having M$_n$ of 18,000 as determined by NMR.

EXAMPLE 24

Copolymerization of 1-hexene and 4-methyl-1-pentene

This example illustrates the preparation of a copolymer of two different olefins. A catalyst was prepared from 0.025 mmole each (indenyl)$_2$HfMe$_2$ and (C$_6$F$_5$)$_3$B.C$_{18}$H$_{37}$OH as prepared in Example 7 in 0.3 mL of dry, oxygen-free toluene. The catalyst was added with stirring to a mixture of 26.8 grams of dry, oxygen-free 1-hexene and 2.6 grams of 4-methyl-1-pentene that had been cooled to 0° C. After four days, the resulting rigid reaction product was dissolved in 50 mL of toluene and poured into 200 mL of methanol to precipitate the product. After drying in a vacuum oven, the polymer weighed 23 grams. NMR analysis disclosed that the polymer contained 5 mole % 4-methyl-1-pentene. According to GPC analysis, the polymer had M$_w$=207,000, M$_n$=62,000 and PD 3.3.

EXAMPLE 25

Preparation of High Molecular Weight Polyhexene

A solution of 0.025 mmole (fluorenyl)$_2$ZrMe$_2$ (as described in Samuel et at. J. Organomet. Chem. 1976, 113, 331) in 0.5 mL of anhydrous toluene was added under N$_2$ to 0.025 mmole (C$_6$F$_5$)$_3$B.C$_{18}$H$_{37}$OH as prepared in Example 7 in 0.5 mL toluene. The resulting catalyst was added to 13.4 grams of 1-dry, oxygen-free 1-hexene at 0° C. The mixture was too thick to stir with a magnetic stirrer after 10 minutes. After approximately 16 hours, the reactor was opened to air and the contents dissolved in hot toluene. This solution was poured with stirring into a large excess of methanol. After drying in a vacuum oven, the precipitated polymer weighed 9.2 grams. Low angle laser light scattering demonstrated that M$_w$ was 2.15×10$^6$. The polydispersity of the polymer was not obtainable because M$_n$ was not independently known. However, polyhexenes were made using the closely related C$_{18}$H$_{37}$OB(C$_6$F$_5$)$_3$$^-$ salts of (cyclopentadienyl)$_2$HfMe$^+$ and (indenyl)$_2$HfMe$^+$. The polymer polydispersities were 2.7 and 2.6 respectively. These are entries 8 and 10 shown in Table 1. Since polydispersity is essentially unaffected by introduction of one fused benzene ring onto the cyclopentadienyl ligand it is believed the polyhexene prepared according to this and Example 26, wherein the ligand bound to the metal has two fused benzene rings, has a polydispersity of about three or less.

EXAMPLE 26

High Molecular Weight Polyhexene

A reaction similar to that Example 25 was carried out using less catalyst such that the monomer:catalyst ratio was 37,700:1. Workup was accomplished by scraping the product from the reactor. From 40.2 grams of 1-hexene was obtained 9.8 grams of polymer. Light scattering analysis revealed that M$_w$ was 3,390,000.

EXAMPLE 27

Polymerization of 1-octadecene

A solution in 0.5 mL toluene of the catalyst prepared as in Example 24 was added with stirring to 13.4 grams of 1-octadecene at 0° C. After approximately 16 hours, the crude product was slurried with warm isopropanol then dried at 160° C./40 Pa (0.3 mm Hg) to give 13.4 grams (85%) of a waxy polymer (m.p. 45° C.). GPC analysis indicated the polymers had a $M_w=154,000$, $M_n=72,000$ and PD=2.14.

EXAMPLE 28

Copolymerization of 1-hexene and 1,13-tetradecadadiene

This example illustrates copolymerization of an olefin and a diolefin. A solution containing 0.025 mmole of the catalyst as prepared as Example 24 was added with stirring to a cold (0° C.) mixture of 26.8 grams (319 mmol) of 1-hexene and 0.17 grams (0.88 retool) of 1,13-$C_{14}H_{26}$, (Shell Co., Houston, Tex.). After approximately 16 hours at this temperature, the insoluble, tough, rubbery polymer was removed from the reactor, cut into small pieces, and then dried at 80° C. under vacuum. The yield was 25.4 grams (94%).

A similar example was run but using instead 0.85 gram of the same diene. The yield of polymer, after vacuum drying, was 25.4 grams (92%).

EXAMPLE 29

Polymerization of Ethylene

In a nitrogen-filled drybox, a solution of 0.05 mmole of (indenyl)$_2$TiMe$_2$ as prepared according in 0.5 mL toluene was added to 0.05 mmole of $(C_6F_5)_3B.C_{18}H_{37}OH$ in 0.5 mL of the same solvent. The flask was attached to a vacuum line, the contents frozen and the nitrogen pumped away. After thawing, ethylene was admitted until the pressure reached 80 kPa (600 mm Hg). The reactor was stirred and more ethylene was added so as to maintain the pressure at approximately 80 kPa during the exothermic polymerization. After ethylene consumption had declined, the now-solid reaction mixture was rinsed from the flask with methanol and air dried. The yield of polyethylene, identified by infrared spectroscopy, was 0.65 gram.

EXAMPLE 30

Preparation of Poly(cyclopentene)

This example illustrates the polymerization of a cyclo-olefin. To 14.7 grams of cyclopentene that had been cooled to 0° C. was added a solution in 0.4 mL of toluene of the catalyst as prepared in Example 24. The reactor was maintained at this temperature and shaken occasionally. After two days, the mixture was filtered. The solid phase, 1.4 grams, was digested with 50 mL of hot toluene to remove lower molecular weight oligomers and then filtered to provide 0.8 gram of a white, insoluble solid. It was identified by infrared spectroscopy and X-ray powder diffraction as poly(cyclopentene).

Various modifications and alterations of this invention will become apparent to those skilled in the art without departing from the scope and spirit of this invention, and it should be understood that this invention is not to be unduly limited to the illustrative embodiments set fourth herein.

We claim:

1. A method of polymerizing olefinically unsaturated monomers comprising:
   (a) contacting at a temperature range within the range of about −90° C. to about 300° C. and at a pressure within the range of about 6.9 kPa to 310 MPa monomers either alone or in combination with one or more monomers in a suitable carrier, solvent or diluent with a catalytically effective amount of the catalyst comprising (a) a neutral borane complex having the formula $(C_6F_5)_3B.(XYH)_q$ and (b) a Group IVB organometallic compound having the formula $(Cp)_pM(R^4)_{(4-p)}$
   wherein M is titanium, zirconium or hafnium;
   X is oxygen, or sulfur;
   p is 1 or 2;
   q is 1 to 3;
   Y is a hydrogen atom, $R^1$—, $(R^2)_3Si$—, or $(R^3)_2C=N$—;
   Cp is a cyclopentadienyl ligand, wherein each carbon atom in the ligand is, independently, substituted with a radical selected from the group consisting of hydrogen, hydrocarbyl radicals, hydrocarbyl-substituted metalloid radicals wherein the metalloid is selected from Group IVA of the periodic table of elements; and wherein the hydrocarbyl and substituted-hydrocarbyl radicals contain 1 to 20 carbon atoms; or one or two pairs of adjacent hydrogen atoms of the cyclopentadienyl ligand are substituted with one or two —(CH)$_4$ groups to form indenyl or fluorenyl radicals, respectively, or moieties with having the general formula $(CH_2)_n$ wherein n is 3 to 6; or further, when p is 2, the cyclopentadienyl ligand is optionally combined into one bidentate ligand molecule by connecting the cyclopentadienyl ligands by an organic or organometalloid group;
   $R^1$ is a hydrocarbyl group containing 1 to 500 carbon atoms, or a hydrocarbyl group containing 1 to 500 carbons and a divalent oxygen or a hydrocarbyl group containing 1 to 500 carbon atoms and a halogen-substituted hydrocarbyl group;
   $R^2$ is independently a linear or branched alkyl group containing 1 to 25 carbon atoms, a phenyl group, or a linear or branched alkyl group or a phenyl group containing a SiO— group;
   $R^3$ is independently a hydrocarbyl group containing 1 to 25 carbon atoms, or a hydrogen atom provided both $R^3$ groups selected are not hydrogen atoms; and
   $R^4$ is independently hydrogen or a hydrocarbyl or substituted-hydrocarbyl group containing from 1 to 20 carbon atoms and wherein the hydrocarbyl or substituted hydrocarbyl group is a straight or branched alkyl group, and if sufficiently large enough to form a ring, a cyclic hydrocarbyl group, an alkyl-substituted cyclohydrocarbyl group, an aromatic group, an aromatic-substituted alkyl group, an alkyl-substituted aromatic group or tri-substituted organometalloid groups of Group IVA elements wherein each hydrocarbyl group on the metalloid contains from 1 to 20 carbon atoms;
   (b) continuing the contacting of step (a) for a sufficient period of time to polymerize at least a portion of said monomers; and
   (c) recovering a polymer product.

2. The method according to claim 1, wherein the olefinically unsaturated monomers have from 2 to 30 carbon atoms.

3. The method according to claim 2, wherein the olefinically unsaturated monomers have from 5 to 10 carbon atoms.

4. The method according to claim 1, wherein the olefinically unsaturated monomers are selected from the group consisting of linear- and branched α-olefins, cyclic olefins, olefins containing an aromatic group, olefins containing silicon or boron, diolefins and mixtures thereof.

5. A method of polymerizing olefinically unsaturated monomers comprising:
   (a) contacting at a temperature range within the range of about −90° C. to about 300° C. and at a pressure within the range of about 6.9 kPa to 31 0 MPa monomers either alone or in combination with one or more monomers in a suitable carrier, solvent or diluent with a catalytically effective amount of the catalyst comprising (a) a borane complex that is an acidic salt wherein the anion portion of the acidic salt has the formula $(C_6F_5)_3B.XY—$ and (b) a Group IVB organometallic compound having the formula $(Cp)_pM(R^4)_{4-p}$ wherein M is titanium, zirconlure or hafnium;
   X is oxygen, or sulfur;
   p is 1 or 2;
   Y is a hydrogen atom, $R^1—$, $(R^2)_3Si—$, or $(R^3)_2C=N—$;
   Cp is a cyclopentadienyl ligand, wherein each carbon atom in the ligand is, independently, substituted with a radical selected from the group consisting of hydrogen, hydrocarbyl radicals, hydrocarbyl-substituted metalloid radicals wherein the metalloid is selected from Group IVA of the periodic table of the elements, and wherein the hydrocarbyl and substituted-hydrocarbyl radicals contain 1 to 20 carbon atoms; or one or two pairs of adjacent hydrogen atoms of the cyclopentadienyl ligand are substituted with one or two $—(CH)_4$ groups to form indenyl or fluorenyl radicals, respectively, or with moieties having the genera( formula $(CH_2)_n$ wherein n is 3 to 6; or further, when p is 2, the cyclopentadienyl ligand is optionally combined into one bidentate ligand molecule by connecting the cyclopentadienyl ligands by an organic or organometalloid group;
   $R^1$ is a hydrocarbyl group containing 1 to 500 carbon atoms, or a hydrocarbyl group containing 1 to 500 carbon atoms and a divalent oxygen or a hydrocarbyl group containing 1 to 500 carbon atoms and a halogen-substituted hydrocarbyl group;
   $R^2$ is independently a linear or branched alkyl group containing 1 to 25 carbon atoms, or a phenyl group, or a linear or branched alkyl group or a phenyl group containing a SiO-group;
   $R^3$ is independently a hydrocarbyl group containing 1 to 25 carbon atoms, or a hydrogen atom provided both $R^3$ groups selected are not hydrogen atoms; and
   $R^4$ is independently hydrogen or a hydrocarbyl or substituted-hydrocarbyl group containing from 1 to 20 carbon atoms and wherein the hydrocarbyl or substituted hydrocarbyl group is a straight or branched alkyl group, and if sufficiently large enough to form a ring, a cyclic hydrocarbyl group, an alkyl-substituted cyclohydrocarbyl group, an aromatic group, an aromatic-substituted alkyl group, an alkyl-substituted aromatic group or trisubstituted organometalloid groups of Group IVA elements wherein each hydrocarbyl group on the metalloid contains from 1 to 20 carbon atoms;
   (b) continuing the contacting of step (a) for a sufficient period of time to polymerize at least a portion of said monomers; and
   (c) recovering a polymer product.

6. The method according to claim 5, wherein the olefinically unsaturated monomers have from 2 to 30 carbon atoms.

7. The method according to claim 6, wherein the olefinically unsaturated monomers have from 5 to 10 carbon atoms.

8. The method according to claim 5, wherein the olefinically unsaturated monomers are selected from the group consisting of linear- and branched α-olefins, cyclic olefins, olefins containing an aromatic group, olefins containing silicon or boron, diolefins and mixtures thereof.

* * * * *